United States Patent [19]

Mitamura et al.

[11] Patent Number: 5,175,354
[45] Date of Patent: Dec. 29, 1992

[54] PROCESS FOR PREPARING 2,6-NAPHTHALENE-DICARBOXYLIC ACID

[75] Inventors: Shuichi Mitamura; Yasuhisa Tsutsumi; Yoshimi Kata; Atsushi Kawada; Naoya Okabayashi, all of Kawasaki, Japan

[73] Assignees: Nippon Steel Chemical Co., Ltd.; Nippon Steel Corporation, both of Tokyo, Japan

[21] Appl. No.: 678,425

[22] Filed: Apr. 1, 1991

[30] Foreign Application Priority Data

Mar. 30, 1990 [JP] Japan .................................. 2-87091
Mar. 30, 1990 [JP] Japan .................................. 2-87092

[51] Int. Cl.$^5$ .......................................... C07C 51/347
[52] U.S. Cl. .................................. 562/481; 562/480; 562/488
[58] Field of Search ........................ 562/487, 488, 480

[56] References Cited

U.S. PATENT DOCUMENTS 3,888,921  6/1975  Yamamoto et al. ................. 562/488
3,954,840  5/1976  Yamashita et al. ............. 562/488 X

FOREIGN PATENT DOCUMENTS 0346029  12/1989  European Pat. Off. .
335235  6/1955  Japan .
37975  12/1955  Japan .
49-27176  7/1974  Japan .
51-47706  12/1976  Japan .

OTHER PUBLICATIONS

Fujishiro et al. *The Chemical Society of Japan*, vol. 62, No. 3 (1989), pp. 786–790.

*Primary Examiner*—Jose G. Dees
*Assistant Examiner*—Vera C. Clarke
*Attorney, Agent, or Firm*—Armstrong & Kubovcik

[57] ABSTRACT

The process of this invention for preparing 2,6-naphthalene-dicarboxylic acid comprises a reaction step (Step A) wherein 2,6-naphthalene-dicarboxylic acid potassium salts consisting of 2,6-naphthalene-dicarboxylic acid dipotassium salt and/or 2,6-naphthalene-dicarboxylic acid monopotassium salt are allowed to react with benzene-carboxylic acids in the presence of water to yield 2,6-naphthalene-dicarboxylic acid and benzene-carboxylic acid potassium salts and a separation step (Step B) wherein the crystallized 2,6-naphthalene-dicarboxylic acid is separated from the benzene-carboxylic acid potassium salts dissolved in the aqueous solution and provides 2,6-naphthalene-dicarboxylic acid, useful as raw material for polymers, at low cost on a commerical scale with recycle of potassium.

5 Claims, 2 Drawing Sheets

PROCESS FOR PREPARING 2,6-NAPHTHALENE-DICARBOXYLIC ACID

FIELD OF THE INVENTION AND RELATED ART STATEMENT

This invention relates to a process for preparing 2,6-naphthalene-dicarboxylic acid which is useful as raw material for functional polymers.

A variety of processes have been proposed for the preparation of 2,6-naphthalene-dicarboxylic acid. A representative example is the so-called Henkel process. According to this process, the potassium salt of α- or β-naphthalene-monocarboxylic acid or the dipotassium salt of a naphthalene-dicarboxylic acid other than 2,6-naphthalene-dicarboxylic acid is heated in an inert gas to yield 2,6-naphthalene-dicarboxylic acid dipotassium salt and the salt thus formed is acidified [Reference should be made to K. Fujishiro and S. Mitamura, Bull. Chem. Soc. Jpn., 62, 786-790 (1989) and literature therein cited.]. In order to practice this process economically, it is necessary to recover potassium efficiently from 2,6-naphthalene-dicarboxylic acid dipotassium salt. The following processes are known for the recovery of potassium. ① The 2,6-naphthalene-dicarboxylic acid dipotassium salt obtained in the Henkel process is treated with a naphthalene-carboxylic acid other than 2,6-naphthalene-dicarboxylic acid to yield 2,6-naphthalene-dicarboxylic acid monopotassium salt and the potassium salt of the naphthalene-carboxylic acid and the former product is disproportionated into 2,6-naphthalene-dicarboxylic acid and its dipotassium salt while the latter is utilized as a reactant in the Henkel process [Japan Tokkyo Koho No. 49-27, 176 (1974)]. ② The 2,6-naphthalene-dicarboxylic acid dipotassium salt obtained in the Henkel process is treated with carbon dioxide gas or sulfur dioxide gas in an aquenous solution to yield 2,6-naphthalene-dicarboxylic acid monopotassium salt and potassium hydrogencarbonate or potassium hydrogensulfite and the former product is disproportionated into 2,6-naphthalene-dicarboxylic acid and its dipotassium salt while the latter is treated with a naphthalene-carboxylic acid other than 2,6-naphthalene-dicarboxylic acid to yield the potassium salt of the naphthalene-carboxylic acid in question, useful as a reactant in the Henkel process [Japan Tokkyo Koho No. 51-47, 706 (1976)].

The aforesaid Henkel process coupled with a process for the recovery of potassium requires naphthalene-carboxylic acids. These acids, however, are produced in limited quantities and expensive and this has made it too costly to practice the Henkel process on a commercial scale.

Reports have been made recently on the preparation of 2,6-naphthalene-dicarboxylic acid dipotassium salt by the reaction of naphthalene with the potassium salt of a benzene-carboxylic acid such as phthalic acid dipotassium salt. (Reference should be made to The 1989 International Chemical Congress of Pacific Basin Societies, Honolulu, December 1989, Abstr., II, No. 405 and European Patent 0346029A1.) Naphthalene and some of benzene-carboxylic acids such as phthalic acid are commercially produced in large quantities and inexpensive and the reported processes are exceedingly useful for application on a commercial scale. For economic reasons, however, it is extremely important here also to establish a process for efficient recovery of potassium. In general, 2,6-naphthalene-dicarboxylic acid is set free from its salt by a strong acid (for example, sulfuric acid, hydrochloric acid, and nitric acid), but it is virtually impossible to recycle the co-produced potassium salt of the strong acid in question as potassium resources for the potassium salt of a benzene-carboxylic acid.

OBJECT AND SUMMARY OF THE INVENTION

The present inventors conducted extensive studies in search of a commercially advantageous process for recycle of potassium while noticing the differences in the acid dissociation constant between benzene-carboxylic acids such as phthalic acid and 2,6-naphthalene-dicarboxylic acid and also the differences in the solubility between the salts of these acids, found a commercially advantageous process for the preparation of 2,6-naphthalene-dicarboxylic acid coupled with the recycle of potassium, and completed this invention.

It is therefore an object of this invention to provide a commercially advantageous process for preparing 2,6-naphthalene-dicarboxylic acid with recycle of the potassium salt.

Another object of this invention is to provide a process for preparing 2,6-naphthalene-dicarboxylic acid which is useful as raw material for polymers at low cost on a commercial scale.

This invention accordingly relates to a process for preparing 2,6-naphthalene-dicarboxylic acid comprising a reaction step (Step A) wherein the potassium salts of 2,6-naphthalene-dicarboxylic acid consisting of 2,6-naphthalene-dicarboxylic acid dipotassium salt and/or 2,6-naphthalene-dicarboxylic acid monopotassium salt are allowed to react with benzene-carboxylic acids of the following general formula (I),

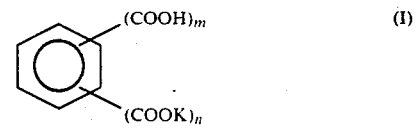

in which m is an integer from 1 to 6, n is an integer from 0 to 5, and m+n is in the range from 1 to 6, in the presence of water to yield 2,6-naphthalene-dicarboxylic acid and benzene-carboxylic acid potassium salts of the following general formula (II),

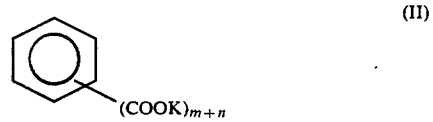

in which m is an integer from 1 to 6, n is an integer from 0 to 5, and m+n is in the range from 1 to 6, and a separation step (Step B) wherein the crystallized 2,6-naphthalene-dicarboxylic acid is separated from the benzene-carboxylic acid potassium salts of the general formula (II) dissolved in the aqueous solution.

This invention also relates to a process for preparing 2,6-naphthalene-dicarboxylic acid comprising a step (Step C) wherein the benzene-carboxylic acid potassium salts of the general formula (II) are recovered from the aqueous solution thereof separated in Step B and allowed to react with naphthalene to yield 2,6-naphthalene-dicarboxylic acid dipotassium salt and the use of said dipotassium salt formed in Step C or of its partial acidification product, namely 2,6-naphthalene-dicarboxylic acid monopotassium salt, as the potassium salts of 2,6-naphthalene-dicarboxylic acid in Step A.

This invention further relates to a process for preparing 2,6-naphthalene-dicarboxylic acid comprising a reaction step (Step D) wherein 2,6-naphthalene-dicarboxylic acid dipotassium salt is allowed to react with phthalic acid monopotassium salt in the presence of water to yield 2,6-naphthalene-dicarboxylic acid monopotassium salt and phthalic acid dipotassium salt, a separation step (Step E) wherein the crystallized 2,6-naphthalene-dicarboxylic acid monopotassium salt is separated from the aqueous solution containing the phthalic acid dipotassium salt, a reaction step (Step F) wherein the 2,6-naphthalene-dicarboxylic acid monopotassium salt separated in Step E is allowed to react with phthalic acid in the presence of water to yield 2,6-naphthalene-dicarboxylic acid and phthalic acid monopotassium salt, a separation step (Step G) wherein the crystallized 2,6-naphthalene-dicarboxylic acid is separated from the aqueous solution containing phthalic acid monopotassium salt, and the use of the phthalic acid monopotassium salt separated in Step G as a reactant in Step D.

This invention still further relates to a process for preparing 2,6-naphthalene-dicarboxylic acid comprising recovering the phthalic acid dipotassium salt from its aqueous solution separated in Step E and using it as reactant in a step (Step C') wherein said phthalic acid dipotassium salt is allowed to react with naphthalene to yield 2,6-naphthalene-dicarboxylic acid dipotassium salt and using said 2,6-naphthalene-dicarboxylic acid dipotassium salt as a reactant in Step D.

Figure 1:
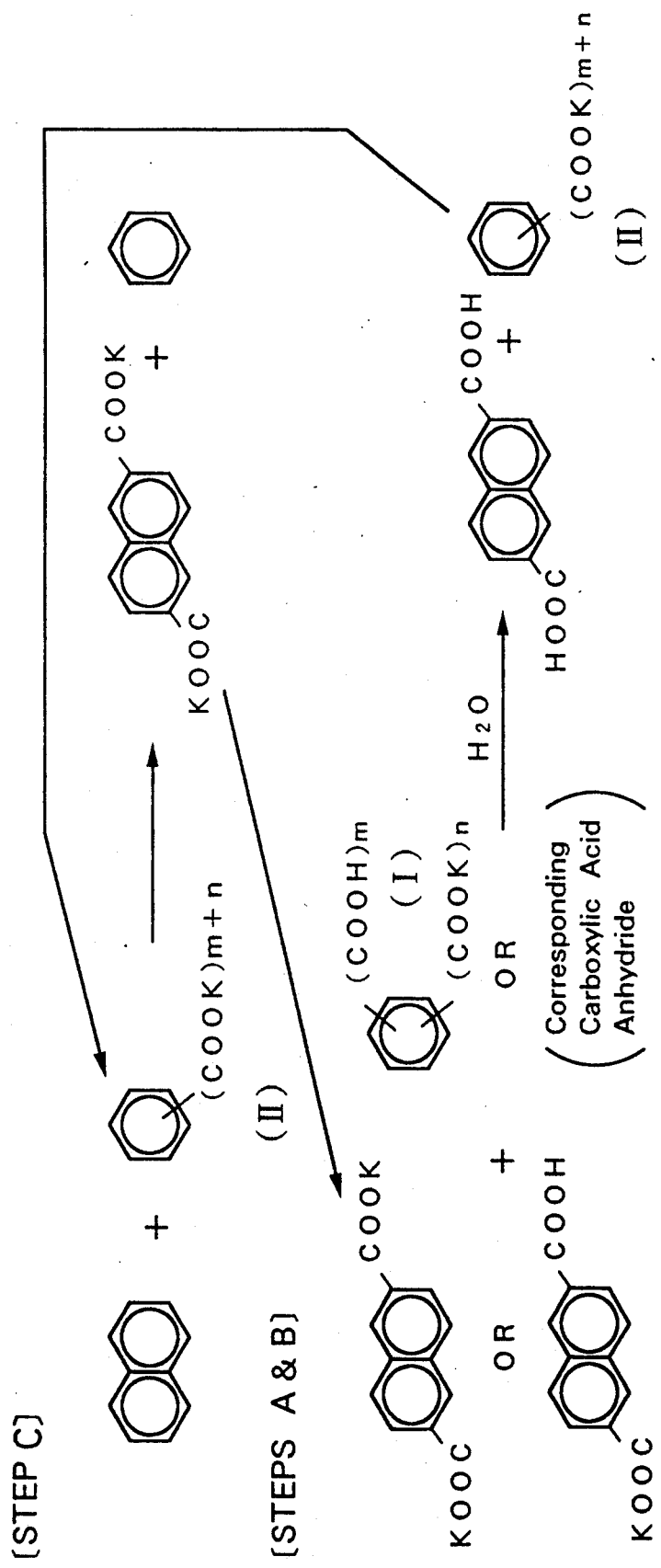
FIG. 1 illustrates the reaction schemes for Steps A, B, and C in the process of this invention for preparing 2,6-naphthalenedicarboxylic acid.
Figure 2:
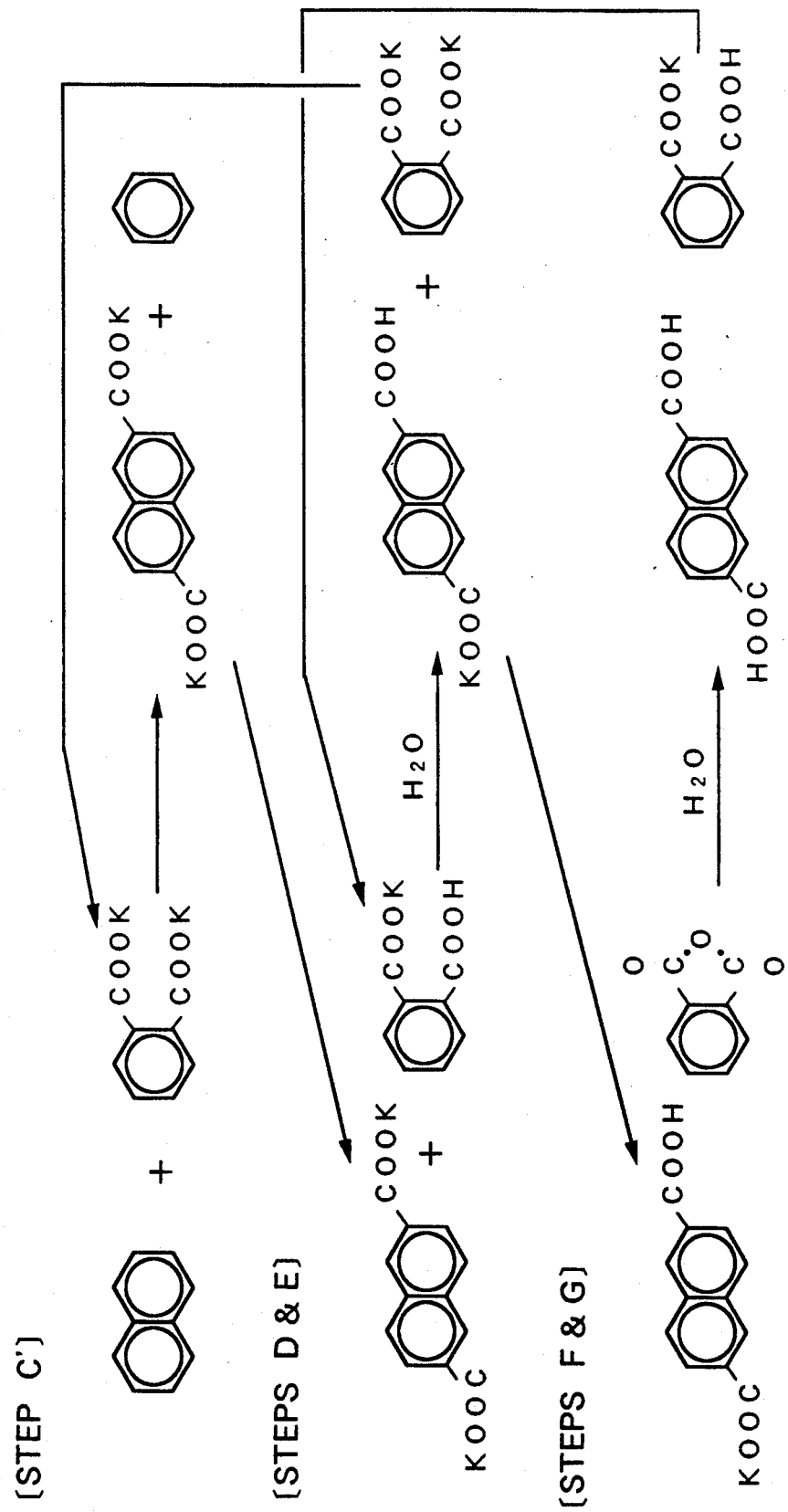
FIG. 2 illustrates the reaction schemes for Steps C', D, E, F, and G in the process of this invention for preparing 2,6-naphthalenedicarboxylic acid.

In Step A, the potassium salts of 2,6-naphthalene-dicarboxylic acid are allowed to react with benzene-carboxylic acids of the general formula (I) [hereinafter often referred to as benzene-carboxylic acids (I)] in the presence of water to yield 2,6-naphthalene-dicarboxylic acid and benzene-carboxylic acid potassium salts of the general formula (II) [hereinafter often referred to as benzene-carboxylic acid potassium salts (II)]. The potassium salts of 2,6-naphthalene-dicarboxylic acid include dipotassium and monopotassium salts and either one or a mixture of the two may be used.

Benzene-carboxylic acids (I) are represented by the general formula (I). In this formula, m is an integer from 1 to 6, n is an integer from 0 to 5, and m+n is an integer from 1 to 6, preferably m is 1 to 4, n is 0 or 1, and m+n is 1 to 4. Such acids include phthalic acid, phthalic acid monopotassium salt, benzoic acid, terephthalic acid, terephthalic acid monopotassium salt, trimellitic acid, trimellitic acid monopotassium salt, pyromellitic acid, and their mixtures. Since the reaction in Step A is carried out in the presence of water, compounds which may react with water to yield benzene-carboxylic acids (I), for example, the acid anhydrides of benzene-carboxylic acids (I), may be used as effectively as the acids cited above. Examples of such acid anhydrides are phthalic anhydride, trimellitic anhydride, trimellitic anhydride monopotassium salt, and pyromellitic dianhydride.

In the cases where the dipotassium salt is used as the potassium salts of 2,6-naphthalene-dicarboxylic acid, the theoretical amount of benzene-carboxylic acids (I) is 2/m mole per 1 mole of 2,6-naphthalene-dicarboxylic acid dipotassium salt. On the other hand, it will be 1/m mole of benzene-carboxylic acids (I) to 1 mole of 2,6-naphthalenedicarboxylic acid monopotassium salt where the monopotassium salt is used as the potassium salts of 2,6-naphthalene-dicarboxylic acid. It is desirable to use the reactants at this ratio and a deviation of ±20% from this ratio is allowable in practice. Benzene-carboxylic acids (I), if used in excess, cannot be converted efficiently to benzene-carboxylic acid potassium salts (II) while the potassium salts of 2,6-naphthalene-dicarboxylic acid remain unchanged and dissolved in water if too little of benzene-carboxylic acids (I) is used.

It is possible that some salts less reactive with the aforesaid benzene-carboxylic acids (I) than the potassium salts of 2,6-naphthalene-dicarboxylic acid are already present dissolved in the reaction system. Even in such a case, benzene-carboxylic acids (I) may be used in the aforesaid amount without ill effect. Such less reactive salts include benzene-carboxylic acid potassium salts such as terephthalic acid dipotassium salt, isophthalic acid dipotassium salt, phthalic acid dipotassium salt, and benzoic acid potassium salt and alkali halides such as potassium iodide, cesium iodide, potassium chloride, cesium chloride, potassium bromide, and cesium bromide. On the other hand, basic compounds more reactive with benzene-carboxylic acids (I) than the potassium salts of 2,6-naphthalene-dicarboxylic acid, for example, dipotassium carbonate, dicesium carbonate, potassium hydroxide, and cesium hydroxide, may be present in the reaction system and selectively consume benzene-carboxylic acids (I) or their corresponding acid anhydrides. In such a case, the more reactive compounds may be neutralized in advance, but they can be dealt with readily by using that much excess of benzene-carboxylic acids (I).

In the aforesaid reaction in Step A, water is used in an amount normal for solvent. The sum of the weight of the potassium salts of 2,6-naphthalene-dicarboxylic acid and that of benzene-carboxylic acids (I), although varying with the kind of salt and acid, is normally 0.001 to 3.00 parts, preferably 0.001 to 2.00 parts, per 1 part of water. A sum of less than 0.001 part by weight requires a large quantity of water, which is economically undesirable. On the other hand, a sum of more than 3.00 parts by weight enhances the concentration of benzene-carboxylic acid potassium salts (II) formed in the reaction above their solubility in water and causes some of them to crystallize out, which makes it difficult to separate them from 2,6-naphthalene-dicarboxylic acid.

In the aforesaid reaction in Step A, the reaction temperature is in the range from 0° to 200° C., preferably from room temperature to 150° C. The reaction time varies with the kind of reactants and the reaction temperature, but it is normally in the range from 0.1 to 100 hours. The higher the reaction temperature, the faster the reaction proceeds and a period of 30 minutes or so is sufficient at 60° C. or higher. A longer period than this does not improve the results to any significant extent. The pressure may be ambient, but the reaction can be carried out under pressure at 100° C. or higher.

The reaction in Step A proceeds in a state of slurry. As the reaction progresses, 2,6-naphthalene-dicarboxylic acid crystallizes out on one hand and benzene-carboxylic acid potassium salts (II) form as dissolved in the reaction solvent, namely water, on the other. It is therefore desirable to stir the reaction mixture efficiently.

After the reaction in Step A, the separation in Step B is effected. The crystals of 2,6-naphthalene-dicarboxylic acid are separated by filtration and, if necessary, washed with water. A study by the present inventors indicates that the benzene-carboxylic acid potassium salts (II) remaining dissolved in the filtrate are useful as a reactant in the aforesaid Step C. The said filtrate is controlled in pH, if needed, and heated to dryness to drive off the water completely. The benzene-carboxylic acid potassium salts (II) obtained as solid residue may be submitted to the aforesaid Step C. The said filtrate may contain the following compounds in addition to the benzene-carboxylic acid potassium salts (II) formed in the aforesaid Step A; benzene-carboxylic acid potassium salts such as terephthalic acid dipotassium salt, isophthalic acid dipotassium salt, phthalic acid dipotassium salt, and benzoic acid potassium salt, alkali halides such as potassium iodide, cesium iodide, potassium chloride, cesium chloride, potassium bromide, and cesium bromide, and the reaction products of benzene-carboxylic acids (I) with basic compounds such as dipotassium carbonate, dicesium carbonate, potassium hydroxide, and cesium hydroxide. As far as the present inventors know, the said filtrate can be heated to dryness without separation of the aforesaid compounds from benzene-carboxylic acid potassium salts (II) and the solid residue thereby obtained can be used as reactant in the aforesaid Step C without ill effect.

The reaction in the aforesaid Step C may be carried out according to the process described in European Patent 0346029A1 cited earlier. The process in question relates to the preparation of 2,6-naphthalene-dicarboxylic acid by the reaction of naphthalene with benzene-carboxylic acid potassium salts (II) in the presence of a catalyst under a carbon dioxide pressure of 10 to 200 kg/cm$^2$.G at 300° to 500° C., said catalyst consisting of a compound or compounds of one or two or more metals selected from group (a) of zinc, cadmium, and thallium, and a compound or compounds of one or two or more metals selected from group (b) of cesium, Group IIa metals, and Group IIIa metals.

After the reaction in Step C, water is added to dissolve therein 2,6-naphthalene-dicarboxylic acid dipotassium salt in the reaction mixture and also an organic solvent such as toluene and xylene is added to dissolve therein the excess naphthalene and the by-product benzene, and the aqueous layer is separated from the organic layer. The compound of group (a) metal in the catalyst for Step C is present as oxide or carbonate insoluble in either water or organic solvents and can be separated readily, together with carbonaceous by-products likewise insoluble in either water or organic solvents, by such means as filtration. The aqueous layer thus separated may contain the following compounds in addition to 2,6-naphthalene-dicarboxylic acid dipotassium salt: benzene-carboxylic acid potassium salts occurring as by-products in the reaction such as terephthalic acid dipotassium salt, isophthalic acid dipotassium salt, phthalic acid dipotassium salt, and benzoic acid potassium salt; water-soluble components of the catalysts and promoters such as potassium iodide, cesium iodide, potassium chloride, cesium chloride, potassium bromide, and cesium bromide; basic compounds occurring as decomposition products such as dipotassium carbonate, dicesium carbonate, potassium hydroxide, and cesium hydroxide. As described above, however, these compounds do not interfere with the aforesaid Step A which follows Step C. Hence, the separated aqueous layer, with or without further concentration, can be fed to Step A as aqueous solution of 2,6-naphthalene-dicarboxylic acid dipotassium salt. The separated aqueous layer, if necessary, is acidified to convert 2,6-dicarboxylic acid dipotassium salt partly to the monopotassium salt and submitted to the reaction in Step A. A weak inorganic or organic acid such as carbon dioxide, sulfur dioxide, and phthalic acid monopotassium salt can be used effectively for the acidification.

Step D provides a desirable example of processes for preparing 2,6-naphthalene-dicarboxylic acid monopotassium salt, one of the reactants in Step A, and relates to the reaction of 2,6-naphthalene-dicarboxylic acid dipotassium salt with phthalic acid monopotassium salt to yield 2,6-naphthalene-dicarboxylic acid monopotassium salt and phthalic acid dipotassium salt. In the reaction of Step D, phthalic acid monopotassium salt is eqimolar ±20%, preferably equimolar, to 2,6-naphthalene-dicarboxylic acid dipotassium salt. At less than equimolar, the conversion of 2,6-naphthalene-dicarboxylic acid dipotassium salt to the monopotassium salt does not proceed quantitatively. Salts less reactive with phthalic acid monopotassium salt than 2,6-naphthalene-dicarboxylic acid dipotassium salt may happen to be present in the reaction system. In such a case, the amount of phthalic acid monopotassium salt can still be equimolar ±20%, preferably equimolar, to 2,6-naphthalene-dicarboxylic acid dipotassium salt. Such salts include the aforesaid compounds in Step A. On the other hand, basic compounds more reactive with phthalic acid monopotassium salt than 2,6-naphthalene-dicarboxylic acid dipotassium salt, for example, dipotassium carbonate, may be present in the reaction system and preferentially consume phthalic acid monopotassium salt. In such a case, phthalic acid monopotassium salt may be used in that much excess. Alternatively, compounds capable of preferentially neutralizing said basic compounds may be used simultaneously. It is desirable that the neutralization products are soluble in water. The compounds suitable for this purpose are benzene-carboxylic acids such as phthalic acid and benzoic acid.

In the reaction of Step D, water is used in an amount normal for solvent. The sum in weight of 2,6-naphthalene-dicarboxylic acid dipotassium salt and phthalic acid monopotassium salt is 0.001 to 3 parts, preferably 0.001 to 1.86 parts, per 1 part of water. A sum of less than 0.001 part by weight requires a large quantity of water, which is not desirable from the economic point of view. On the other hand, at a sum of more than 1.86 parts by weight, phthalic acid dipotassium salt formed in the reaction attains a concentration higher than its solubility in water and crystallizes out, making its separation difficult from 2,6-naphthalene-dicarboxylic acid monopotassium salt.

In the reaction of Step D, the reaction temperture is in the range from 0° C. to 200° C., preferably from room temperature to 150° C. As 2,6-naphthalene-dicarboxylic acid dipotassium salt and phthalic acid monopotassium salt are both easily soluble in water, they react sufficiently at room temperature. The reaction time, although varying with the reaction temperature, is normally in the range from 0.1 to 100 hours. The higher the temperature, the faster the reaction progresses. One hour or so at room temperature or 30 minutes or so at 30° C. or above will be sufficient and a longer time than this will not produce any significant difference in the results. The reaction may be carried out at ambient pressure or at 100° C. or higher under pressure.

The reaction of Step D proceeds in a state of slurry. As the reaction advances, 2,6-naphthalene-dicarboxylic acid monopotassium salt crystallizes out while phthalic acid dipotassium salt forms as dissolved in the solvent water. It is therefore desirable to stir the reaction mixture efficiently.

After the reaction of Step D, the separation of Step E is effected. The crystals may be filtered as they are. In the cases where the reaction of Step D is carried out under heat, however, the filtration is desirably effected after cooling the reaction mixture to room temperature. The higher the temperature during filtration, the more 2,6-naphthalene-dicarboxylic acid monopotassium salt dissolves in water and the lower its yield becomes. The crystals of 2,6-naphthalene-dicarboxylic acid monopotassium salt are washed with water, if necessary, and used as a reactant in Step F.

Step F relates to the reaction of 2,6-naphthalene-dicarboxylic acid monopotassium salt with phthalic acid to yield 2,6-naphthalene-dicarboxylic acid and phthalic acid monpotassium salt. In stead of Phthalic acid, its anhydride can be also used. Phthalic acid or its anhydride may be used here in an amount equimolar ±10%, preferably equimolar, to 2,6-naphthalene-dicarboxylic acid monopotassium salt. With less than the equimolar quantity, it is not possible to convert 2,6-naphthalene-dicarboxylic acid monopotassium salt to 2,6-naphthalene-dicarboxylic acid quantitatively. With more than the equimolar quantity, the unreacted phthalic acid crystallizes out and makes its separation from 2,6-naphthalene-dicarboxylic acid difficult.

In the reaction of Step F, water is used in an amount normal for solvent. The sum in weight of 2,6-naphthalene-dicarboxylic acid monopotassium salt and phthalic acid or its anhydride is in the range from 0.001 to 3 parts, preferably from 0.001 to 0.25 part, per 1 part of water. A sum of less than 0.001 part by weight requires a large quantity of water, which is undesirable from the economic point of view. On the other hand, at a sum of more than 0.25 part by weight, phthalic acid monopotassium salt reaches a concentration above its solubility in water and crystallizes out, which makes its separation from 2,6-naphthalene-dicarboxylic acid difficult.

In the reaction of Step F, the reaction temperature is in the range from 0° C. to 200° C., preferably from 40° C. to 150° C. As 2,6-naphthalene-dicarboxylic acid monopotassium salt and phthalic acid or its anhydride are both sparingly soluble in water, their reaction is hard to proceed at 40° C. or below. The reaction time, although varying with the reaction temperature, is normally in the range from 0.1 to 100 hours. The higher the temperature, the faster the reaction progresses. A period of 30 minutes or so at 60° C. or above is sufficient and a longer time than this will not produce any significant difference in the results. The reaction may be carried out at ambient pressure or at 100° C. or above under pressure.

The reaction of Step F proceeds in a state of slurry. As the reaction progresses, 2,6-naphthalene-dicarboxylic acid crystallizes out while phthalic acid monopotassium salt forms as dissolved in the reaction solvent water. It is therefore desirable to stir the reaction mixture efficiently.

After the reaction of Step F, the separation of Step G is effected. The filtered crystals of 2,6-naphthalene-dicarboxylic acid are washed with water if necessary. Phthalic acid monopotassium salt dissolved in the filtrate can be used as a reactant in Step D. It is possible to recover phthalic acid monopotassium salt from the filtrate by removal of water or other means, but it is preferable to submit the salt as dissolved in the filtrate to the reaction of Step D for operational simplicity.

Studies of the present inventors indicate that phthalic acid dipotassium salt present in the filtrate separated from 2,6-naphthalene-dicarboxylic acid monopotassium salt in Step E may be used as reactant in Step C'. The filtrate is controlled in its pH, if needed, and heated to dryness in order to remove the water completely and obtain phthalic acid dipotassium salt as solid residue. The solid salt is then submitted to the reaction of Step C'. The filtrate may contain the following compounds in addition to phthalic acid dipotassium salt formed in the reaction of Step D; benzene-carboxylic acid potassium salts such as terephthalic acid dipotassium salt, isophthalic acid dipotassium salt, phthalic acid dipotassium salt, and benzoic acid potassium salt and alkali halides such as potassium iodide, cesium iodide, potassium chloride, cesium chloride, potassium bromide, and cesium bromide. As far as the present inventors know, however, it is allowable to heat the filtrate in question to dryness without separating these compounds from phthalic acid dipotassium salt and submit the solid residue as a reactant to the reaction of Step C'.

The reaction of Step C' may be carried out as in the aforesaid Step C. This reaction yields 2,6-naphthalene-dicarboxylic acid dipotassium salt, which can be used as a reactant in Step D.

DETAILED DESCRIPTION OF THE PREFERRED EMBODIMENTS

This invention will be explained in detail with reference to the accompanying examples.

EXAMPLE 1

A suspension of 5.84 g. of 2,6-naphthalene-dicarboxylic acid dipotassium salt (NDCADK) and 2.96 g. of phthalic anhydride (PA) in 50 ml. of water was heated at reflux temperature (100° C.) for 120 minutes with stirring. After the reaction, the reaction mixture was cooled to room temperature, the precipitates were collected by filtration, washed with water, and dried to yield 4.11 g. of crystals. The crystals and the filtrate were submitted to HPLC (Hight Performance Liquid Chromatograph) analysis and acid value measurement and the following results were obtained.

| Crystals | |
|---|---|
| 2,6-Naphthalene-dicarboxylic acid (NDCA) recovery | 95.9 mol % |
| PA' content | <1 mol % |
| [PA': phthalic acid and/or corresponding potassium salt] | |
| Potassium (K) content (based on charged potassium) | 0 mol % |
| Filtrate | |
| Phthalic acid dipotassium salt (PADK) recovery | >99 mol % |

These quantities were calculated as follows:

$$\text{NDCA recovery (mol \%)} = \frac{\text{NDCA in crystals (mol)}}{\text{NDCADK charged (mol)}} \times 100$$

PA' content (mol %) =

$$\frac{\text{PA' in crystals (mol)}}{\text{Sum of NDCA and PA' in crystals (mol)}} \times 100$$

-continued

K content (mol %) =

$$\frac{[(-COOH + -COOK)^* - (-COOH)^{**}] \text{ (mol)}}{K \text{ charged (mol)}} \times 100$$

$$\text{PADK recovery (mol \%)} = \frac{\text{PADK in filtrate (mol)}}{\text{PA charged (mol)}} \times 100$$

*Sum of carboxyl groups calculated from NDCA and PA' in crystals
**Free carboxyl groups in crystals obtained by acid value measurement

EXAMPLES 2-5

Experiments were conducted in the same conditions as in Example 1 except for the amount of water as shown in Table 1 and the results are shown in Table 1.

TABLE 1

| Ex. | Water (ml.) | Amt. (g.) | Crystals NDCA recovery (mol %) | PA' content (mol %) | K content (mol %) | Filtrate PADK recovery (mol %) |
|---|---|---|---|---|---|---|
| 2 | 15 | 4.50 | 96.1 | <1 | 14.6 | >99 |
| 3 | 80 | 3.96 | 92.3 | <1 | 1.7 | >99 |
| 4 | 100 | 4.16 | 96.1 | 2.7 | 2.5 | 97.2 |
| 5 | 170 | 4.11 | 96.1 | <1 | 0 | >99 |

(Note)
The NDCA recovery, PA' content, K content, and PADK receovery were calculated as in Example 1.

EXAMPLES 6-10

Experiments were conducted in the same conditions as in Example 1 except for the reaction temperature and the reaction time shown in Table 2 and the results are shown in Table 2.

TABLE 2

| Ex. | Reaction temp. (°C.) | Reaction time (min.) | Amt. (g.) | Crystals NDCA recovery (mol %) | PA' content (mol %) | K content (mol %) | Filtrate PADK recovery (mol %) |
|---|---|---|---|---|---|---|---|
| 6 | 80 | 120 | 4.30 | 97.1 | 2.8 | 2.2 | 97.3 |
| 7 | 60 | 120 | 4.17 | 94.1 | 3.1 | 1.3 | 97.2 |
| 8 | 40 | 120 | 4.30 | 93.1 | 6.9 | 6.9 | 93.0 |
| 9 | 100 | 30 | 4.38 | 99.1 | <1 | 4.8 | >99 |
| 10 | 80 | 30 | 4.25 | 97.9 | <1 | 4.8 | >99 |

(Note)
The NDCA recovery, PA' content, K content, and PADK receovery were calculated as in Example 1.

EXAMPLES 11-14

Experiments were conducted as in Example 1 except using benzenecarboxylic acids (I) instead of phthalic anhydride, as shown in Table 3 and the results are shown in Table 3.

TABLE 3

| Ex. | Benzene-carboxylic acids (I) Kind | Amt. (g.) | Crystals Amt. (g.) | NDCA recovery (mol %) | BCA cont. (mol %) | K cont. (mol %) | Filtrate BCAK recovery (mol %) |
|---|---|---|---|---|---|---|---|
| 11 | BA | 2.44 | 4.30 | 98.7 | 2.1 | 4.8 | 98.9 |
| 12 | IPA | 3.32 | 4.36 | 99.4 | 2.0 | 0 | 98.0 |
| 13 | TMA | 3.84 | 4.23 | 99.5 | <1 | 0 | >99 |
| 14 | PMA | 4.36 | 4.21 | 99.0 | <1 | 2.8 | >99 |

(Notes)
BA: Benzoic acid
IPA: Isophthalic acid
TMA: Trimellitic acid
PMA: Pyromellitic acid BCA: Benzene-carboxylic acids (I) and/or benzene-carboxylic acid potassium salts (II)
BCAK: Benzene-carboxylic acid potassium salts (II)
The NDCA recovery was calculated as in Example 1.
The BCA content, K content and BCAK recovery were calculated as follows.

$$\text{BCA content (mol \%)} = \frac{\text{BCA in crystals (mol)}}{\text{Sum of NDCA and BCA in crystals (mol)}} \times 100$$

$$\text{K content (mol \%)} = \frac{[(-COOK + -COOH)^* - (-COOH)^{**}] \text{(mol)}}{\text{K charged (mol)}} \times 100$$

*Total carboxyl groups calculated from NDCA and BCA in crystals
**Free carboxyl groups in crystals obtained by acid value measurement $$\text{BCAK recovery (mol \%)} = \frac{\text{BCAK in filtrate (mol)}}{\text{Benzene-carboxylic acids (I) charged (mol)}} \times 100$$

EXAMPLE 15

The procedure of Example 1 was followed except using a suspension of 4.57 g. of 2,6-naphthalene-dicarboxylic acid monopotassium salt (NDCAK) and 3.67 g. of phthalic acid monopotassium salt (PAK) in 50 ml. of water and 3.86 g. of crystals was obtained. The crystals and the filtrate were submitted to HPLC analysis and acid value measurement and the following results were obtained.

| Crystals | |
|---|---|
| NDCA recovery | 99 mol % |
| PA' content | <1 mol % |
| K content | 5.7 mol % |
| Filtrate | |
| PADK recovery | >99 mol % |

The NDCA recovery, PA' content, and K content were calculated as in Example 1.
The PADK recovery was calculated as follows.

$$\text{PADK recovery (mol \%)} = \frac{\text{PADK in filtrate (mol)}}{\text{PAK charged (mol)}} \times 100$$

EXAMPLE 16

A mixture of 11.2 g. of phthalic acid dipotassium salt, 47.5 g. of naphthalene, 2.71 g. of $CdI_2$, and 1.92 g. of CsI was heated at 400° C. under carbon dioxide gas pressure of 65 kg/cm². G for 18 hours with stirring. The reaction mixture was dissolved in water and toluene, the aqueous layer was separated and concentrated to dryness, and the residue was found by HPLC analysis to contain 6.76 g. of 2,6-naphthalene-dicarboxylic acid dipotassium salt, 1.03 g. of terephthalic acid dipotassium salt, 1.47 g. of dipotassium carbonate, and others. The residue and 4.21 g. of phthalic anhydride were suspended in 100 ml. of water, and the suspension was stirred at reflux temperature for 120 minutes, cooled to room temperature, and filtered to separate the precipitates. The precipitates were washed with water and dried to yield 5.4 g. of crystals. The crystals and the filtrate were submitted to HPLC analysis and acid value measurement and the following results were obtained.

| Crystals | |
|---|---|
| NDCA recovery | 98.2 mol % |
| BCA content | 2.8 mol % |
| K content | 3.0 mol % |
| Filtrate | |
| PADK recovery | >99 mol % |

The NDCA recovery and PADK recovery were calculated as in Example 1 and the BCA content and K content were calculated as in Examples 11 to 14.

The filtrate obtained above was mixed with 0.92 g. of phthalic anhydride and 2.04 g. of Cd phthalate, and concentrated to dryness. The residue was mixed with 4.75 g. of naphthalene, and the mixture was heated at 400° C. under carbon dioxide gas pressure of 65 kg/cm². G for 18 hours with stirring. The reaction mixture was dissolved in water and toluene, the aqueous layer was separated and concentrated to dryness, and the residue was found by HPLC analysis to contain 6.61 g. of 2,6-naphthalene-dicarboxylic acid dipotassium salt, 1.12 g. of terephthalic acid dipotassium salt, 1.39 g. of dipotassium carbonate, and others. This residue is usable as a reactant in Step A.

EXAMPLE 17

A suspension of 5.84 g. of 2,6-naphthalene-dicarboxylic acid dipotassium salt (NDCADK) and 4.08 g. of phthalic acid monopotassium salt (PAK) in 50 ml. of water was stirred at 30° C. for 120 minutes, cooled to room temperature, and filtered. The precipitates thereby obtained were washed with water and dried to give 4.94 g. of crystals. The crystals and the filtrate were submitted to HPLC analysis and acid value measurement and the following results were obtained.

| Crystals | |
|---|---|
| 2,6-naphthalene-dicarboxylic acid monopotassium salt (NDCAK) recovery | 97.0 mol % |
| PA' content | 1.7 mol % |
| Filtrate | |
| PADK recovery | 95.7 mol % |

The NDCAK recovery and PA' content were calculated as follows.

$$NDCAK \text{ recovery (mol \%)} = \frac{NDCAK \text{ in crystals (mol)}}{NDCADK \text{ charged (mol \%)}} \times 100$$

$$PA' \text{ content (mol \%)} = \frac{PA' \text{ in crystals (mol)}}{\text{Sum of NDCADK and PA' in crystals (mol)}} \times 100$$

The PADK recovery was calculated as in Example 15.

The crystals obtained here, 4.00 g. out of 4.94 g., were suspended in 50 ml. of water together with 2.33 g. of phthalic anhydride (PA), the suspension was stirred at reflux temperature for 120 minutes, cooled to room temperature, and filtered. The precipitates thereby obtained were washed with water and dried to yield 3.47 g. of crystals. The crystals and the filtrate were submitted to HPLC analysis and acid value measurement and the following results were obtained.

| Crystals | |
|---|---|
| NDCA recovery | >99 mol % |
| PA' content | <1 mol % |
| K content | 0 mol % |
| Filtrate | |
| Phthalic acid monopotassium salt (PAK) recovery | >99 mol % |

The PA' content and the K content were calculated as in Example 1.

$$NDCA \text{ recovery (mol \%)} = \frac{NDCA \text{ in crystals (mol)}}{NDCAK \text{ charged (mol)}} \times 100$$

$$PAK \text{ recovery (mol \%)} = \frac{PAK \text{ in filtrate (mol)}}{PA \text{ charged (mol)}} \times 100$$

The use of this filtrate as phthalic acid monopotassium salt in Step D yielded practically the same results as above.

EXAMPLE 18

A suspension of 5.84 g. of 2,6-naphthalene-dicarboxylic acid dipotassium salt (NDCADK) and 4.08 g. of phthalic acid monopotassium salt in 50 ml. of water was stirred at reflux temperature for 120 minutes, cooled to room temperature, and filtered. The precipitates thereby obtained were washed with water and dried to yield 4.85 g. of crystals. The crystals and the filtrate were submitted to HPLC analysis and acid value measurement and the following results were obtained.

| Crystals | |
|---|---|
| NDCAK recovery | 98.7 mol % |
| PA' content | <1 mol % |
| Filtrate | |
| PADK recovery | 96.9 mol % |

The crystals obtained above, 4.57 g. out of 4.85 g., were suspended in 50 ml. of water together with 2.66 g. of phthalic anhydride (PA), the suspension was stirred at reflux temperature for 120 minutes, cooled to room temperature, and filtered. The precipitates thereby obtained were washed with water and dried to yield 3.99 g. of crystals. The crystals and the filtrate were submitted to HPLC analysis and acid value measurement and the following results were obtained.

| Crystals | |
|---|---|
| NDCA recovery | >99 mol % |
| PA' content | 3.0 mol % |
| K content | 5.86 mol % |
| Filtrate | |
| PAK recovery | 96.8 mol % |

The use of this filtrate as phthalic acid monopotassium salt in Step D yielded practically the same results as above.

The NDCAK recovery, PA' content, PADK recovery, NDCA recovery, K content, and PAK recovery were calculated as in Example 17.

EXAMPLE 19

A mixture of 11.2 g. of phthalic acid dipotassium salt, 47.5 g. of naphthalene, 2.71 g. of $CdI_2$, and 1.92 g. of CsI was heated at 400° C. under carbon dioxide gas pressure of 65 kg/cm$^2$.G for 18 hours with stirring. The reaction mixture was dissolved in water and toluene. The aqueous layer thereby separated was concentrated to dryness, and the residue was found by HPLC analysis to contain 6.76 g. of 2,6-naphthalenedicarboxylic acid dipotassium salt, 1.03 g. of terephthalic acid dipotassium salt, 1.47 g. of dipotassium carbonate, and others. The residue, 4.72 g. of phthalic acid monopotassium salt (PAK), and 0.79 g. of phthalic anhydride were suspended in 100 ml. of water, and the suspension was stirred at reflux temperature for 120 minutes, cooled to room temperature, and filtered. The precipitates thereby obtained were washed with water and dried to yield 6.0 g. of crystals. The crystals and the filtrate were submitted to HPLC analysis and acid value measurement and the following results were obtained.

| Crystals | |
|---|---|
| NDCAK recovery | 95.9 mol % |
| BCA content | <1 mol % |
| Filtrate | |
| PADK recovery | >99 mol % |

The filtrate obtained above was mixed with 0.92 g. of phthalic anhydride and 2.04 g. of cadmium phthalate, concentrated to dryness. The residue was mixed with 47.5 g. of naphthalene, and heated at 400° C. under carbon dioxide gas pressure of 65 kg/cm$^2$.G for 18 hours with stirring. The reaction mixture was dissolved in toluene and water, the aqueous layer was separated and concentrated to dryness, and the residue was found by HPLC analysis to contain 6.56 g. of 2,6-naphthalenedicarboxylic acid dipotassium salt, 1.14 g. of terephthalic acid dipotassium salt, 1.34 g. of dipotassium carbonate, and others.

The crystals obtained above, 4.0 g. out of 6.0 g., were suspended in 50 ml. of water together with 2.26 g. of phthalic anhydride (PA), and the suspension was stirred at reflux temperature for 120 minutes, cooled to room temperature, and filtered. The precipitates thereby obtained were washed with water and dried to yield 3.39 g. of crystals. The crystals and the filtrate were submitted to HPLC analysis and acid value measurement and the following results were obtained.

| Crystals | |
|---|---|
| NDCA recovery | >99 mol % |
| BCA content | 1.3 mol % |
| K content | 3.6 mol % |
| Filtrate | |
| PAK recovery | >99 mol % |

The use of the filtrate as phthalic acid monopotassium salt in Step D yielded practically the same results as above.

The NDCAK recovery, PADK recovery, NDCA recovery, and PAK recovery were calculated as in Example 17 and the K content and BCA content were calculated as in Example 16.

What is claimed is:

1. A process for preparing 2,6-naphthalenedicarboxylic acid which comprises
   a) reacting at least one of 2,6-naphthalenedicarboxylic acid dipotassium salt and 2,6-naphthalenedicarboxylic acid monopotassium salt with a benzenecarboxylic acid of the formula

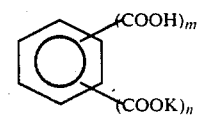

wherein m is an integer from 1 to 6, n is an integer from 0 to 5, and m + n is 1 to 6, in the presence of water at a temperature of 0°-200° C. to yield solid 2,6-naphthalenedicarboxylic acid and an aqueous solution of a benzenecarboxylic acid potassium salt of the formula

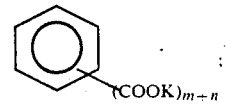

b) separating the solid 2,6-naphthalenedicarboxylic acid from the aqueous solution; c) recovering the benzenecarboxylic acid potassium salt from the aqueous solution; d) reacting the benzenecarboxylic acid potassium salt with naphthalene to yield 2,6-naphthalenedicarboxylic acid dipotassium salt; and e) recycling the 2,6-naphthalene-dicarboxylic acid dipotassium salt to step a).

2. A process according to claim 1, wherein a portion of the 2,6-naphthalenedicarboxylic acid dipotassium salt formed in step d) is acidified to form 2,6-naphthalenedicarboxylic acid monopotassium salt prior to being recycled to step a).

3. A process for preparing 2,6-naphthalenedicarboxylic acid according to claim 1, wherein the benzenecarboxylic acid in step a) is phthalic acid, phthalic acid monopotassium salt, benzoic acid, terephthalic acid, terephthalic acid monopotassium salt, trimellitic acid, trimellitic acid monopotassium salt or pyromellitic acid.

4. A process for preparing 2,6-naphthalenedicarboxylic acid which comprises a) reacting 2,6-naphthalenedicarboxylic acid dipotassium salt with phthalic acid monopotassium salt in the presence of water at a temperature of 0°-200° C. to yield solid 2,6-naphthalenedicarboxylic acid monopotassium salt and an aqueous solution of a phthalic acid dipotassium salt; b) separating the solid 2,6-naphthalenedicarboxylic acid monopotassium salt from the aqueous solution containing phthalic acid dipotassium salt; c) reacting the 2,6-naphthalenedicarboxylic acid monopotassium salt with phthalic acid in the presence of water at 0°–200° C. to yield solid 2,6-naphthalenedicarboxylic acid and an aqueous solution of phthalic acid monopotassium salt; d) separating solid 2,6-naphthalenedicarboxylic acid from the aqueous solution containing phthalic acid monopotassium salt; and e) recycyling the aqueous solution containing phthalic acid monopotassium salt to step a).

5. A process for preparing 2,6-naphthalenedicarboxylic acid according to claim 4, wherein the phthalic acid dipotassium salt is recovered from the aqueous solution containing said salt, the recovered salt is reacted with naphthalene to yield 2,6-naphthalenedicarboxylic acid dipotassium salt and the 2,6-naphthalenedicarboxylic acid dipotassium salt so produced is returned to step a) of claim 4.

* * * * *